(12) United States Patent
Nishida et al.

(10) Patent No.: US 7,795,222 B2
(45) Date of Patent: Sep. 14, 2010

(54) METHODS FOR TREATING A CORNEAL DISORDER AND PROMOTING SKIN WOUND HEALING

(75) Inventors: Teruo Nishida, 8-4, Asutopia 6-chome, Ube-shi, Yamaguchi 755-0152 (JP); Makoto Inui, Ube (JP); Masatsugu Nakamura, Ikoma (JP)

(73) Assignees: Santen Pharmaceutical Co., Ltd., Osaka (JP); Teruo Nishida, Ube-shi, Yamaguchi (JP)

( * ) Notice: Subject to any disclaimer, the term of this patent is extended or adjusted under 35 U.S.C. 154(b) by 573 days.

(21) Appl. No.: 11/725,761

(22) Filed: Mar. 20, 2007

(65) Prior Publication Data

US 2009/0005317 A1 Jan. 1, 2009

Related U.S. Application Data

(62) Division of application No. 10/497,628, filed as application No. PCT/JP02/12632 on Dec. 3, 2002, now Pat. No. 7,232,881.

(30) Foreign Application Priority Data

Dec. 3, 2001 (JP) .............................. 2001-368103

(51) Int. Cl.
 A61K 38/10 (2006.01)
 A61K 38/07 (2006.01)
 A61K 38/06 (2006.01)

(52) U.S. Cl. .............................. 514/14; 514/16; 514/17; 514/18

(58) Field of Classification Search ........................ None
See application file for complete search history.

(56) References Cited

U.S. PATENT DOCUMENTS

| | | | |
|---|---|---|---|
| 4,885,163 A | 12/1989 | Shaar et al. | |
| 5,427,778 A | 6/1995 | Finkenaur et al. | |
| 6,221,846 B1 | 4/2001 | Nishida et al. | |
| 6,310,040 B1 | 10/2001 | Bozyczko-Coyne et al. | |

FOREIGN PATENT DOCUMENTS

| | | |
|---|---|---|
| EP | 0 914 827 A1 | 5/1999 |
| JP | 63-233925 A | 9/1988 |
| JP | 2-112 A | 1/1990 |
| JP | 5-25001 A | 2/1993 |
| JP | 6-48901 A | 2/1994 |
| JP | 7-500839 A | 1/1995 |
| JP | 10-17489 A | 1/1998 |
| WO | WO 93/08826 A1 | 5/1993 |
| WO | WO 93/23067 A1 | 11/1993 |
| WO | WO 95/13087 A1 | 5/1995 |
| WO | WO 97/49419 A1 | 12/1997 |

OTHER PUBLICATIONS

*Jpn. J. Clinic Ophthalmol.*, 46, pp. 738-743 (1992).
C. Katakami, "A New Treatment for Corneal Epithelial Defects Using Fibronectin, EGF and Hyaluronic Acid", *Jpn. J. Ophthalm. Surg.*, 5, pp. 719-727 (1992).
N. Takasu, "Insulin—like Growth Factor I Stimulates Inositol Phosphate Accumulation, . . . ", *J. Biol. Chem.*, 264, pp. 18485-18488 (1989).
P.V. Pedone et al, "Mono-and bi—allelic expression of insulin—like growth factor II gene in human muscle tumors", *Hum. Mol. Genet.*, 3, pp. 1117-1121 (1994).
Y. Inoue et al, "The Sequential Changes of Substance P During Acute Herpetic Keratitis in Mice", *J. Jpn. Ophthalmol. Soc.*, 91, pp. 982-987 (1987) (with English language Abstract).
T. Katayama, "Ocular Inflammation and Neuropeptides in Rabbit Ocular Tissue", *J. Jpn. Ophthalmol. Soc.*, 92, pp. 448-452 (1988) (with English language Abstract).
"analog". Dorlands Illustrated Medical Dictionary. <http://www.mercksource.com/pp/us/cns/cns_health_library_frame.jsp?pg=/pp/us/cns/cns_hl_dorlands.jsp?pg=/pp/us/common/dorlands/dorland/dmd_a-b_00.htm&cd=d>, accessed Jan. 17, 2006. Last indexed Aug. 31, 2002.
Masatugu Nakamura, Tai-ichiro Chikama, Teruo Nishida, "Synergistic effect with Phe-Gly-Leu-Met-$NH_2$ of the C-terminal of substance P and insulin-like growth factor-1 on epithelial wound healing of rabbit cornea," *British Journal of Pharmacology*, vol. 127, No. 2, May 1999, pp. 489-497.
Tai-ichiro Chikama et al., "Treatment of neurotrophic keratopathy with substance-P-derived peptide (FGLM) and insulin-like growth factor I," *The Lancet*, Lancet Limited, London, GB, vol. 351, No. 9118, Jun. 13, 1998, pp. 1783-1788.

*Primary Examiner*—Andrew D Kosar
(74) *Attorney, Agent, or Firm*—Frishauf, Holtz, Goodman & Chick, P.C.

(57) ABSTRACT

A method for treating a corneal disorder or for promoting skin wound healing comprising administering to a patient in need thereof a composition containing pharmaceutically effective amounts of (i) a first peptide comprising an amino acid sequence containing the following consecutive amino acids: Ser-Ser-Ser-Arg (SEQ ID NO: 1), or an analog thereof or a pharmaceutically acceptable salt thereof and (ii) a second peptide comprising an amino acid sequence containing the following consecutive amino acids with a terminal —$NH_2$ group: Phe-Gly-Leu-Met-$NH_2$ (SEQ ID NO: 2), or an analog thereof or a pharmaceutically acceptable salt thereof, together with a pharmaceutically acceptable carrier.

6 Claims, No Drawings

SEQUENCE LISTING

```
<160> NUMBER OF SEQ ID NOS: 17

<210> SEQ ID NO 1
<211> LENGTH: 4
<212> TYPE: PRT
<213> ORGANISM: Human

<400> SEQUENCE: 1

Ser Ser Ser Arg
1

<210> SEQ ID NO 2
<211> LENGTH: 4
<212> TYPE: PRT
<213> ORGANISM: Human

<400> SEQUENCE: 2

Phe Gly Leu Met
1

<210> SEQ ID NO 3
<211> LENGTH: 12
<212> TYPE: PRT
<213> ORGANISM: Human

<400> SEQUENCE: 3

Gly Tyr Gly Ser Ser Ser Arg Arg Ala Pro Gln Thr
1               5                   10
```

```
<210> SEQ ID NO 4
<211> LENGTH: 8
<212> TYPE: PRT
<213> ORGANISM: Human

<400> SEQUENCE: 4

Gly Ser Ser Ser Arg Arg Ala Pro
1               5

<210> SEQ ID NO 5
<211> LENGTH: 5
<212> TYPE: PRT
<213> ORGANISM: Human

<400> SEQUENCE: 5

Ser Ser Ser Arg Arg
1               5

<210> SEQ ID NO 6
<211> LENGTH: 5
<212> TYPE: PRT
<213> ORGANISM: Human

<400> SEQUENCE: 6

Gly Ser Ser Ser Arg
1               5

<210> SEQ ID NO 7
<211> LENGTH: 6
<212> TYPE: PRT
<213> ORGANISM: Human

<400> SEQUENCE: 7

Gly Ser Ser Ser Arg Arg
1               5

<210> SEQ ID NO 8
<211> LENGTH: 8
<212> TYPE: PRT
<213> ORGANISM: Human

<400> SEQUENCE: 8

Ala Ser Ser Ser Arg Arg Ala Pro
1               5

<210> SEQ ID NO 9
<211> LENGTH: 8
<212> TYPE: PRT
<213> ORGANISM: Human

<400> SEQUENCE: 9

Gly Ser Ser Ser Arg Ala Ala Pro
1               5

<210> SEQ ID NO 10
<211> LENGTH: 9
<212> TYPE: PRT
<213> ORGANISM: Human

<400> SEQUENCE: 10

Gly Ser Ser Ser Arg Ala Ala Ala Pro
1               5
```

```
<210> SEQ ID NO 11
<211> LENGTH: 12
<212> TYPE: PRT
<213> ORGANISM: Human

<400> SEQUENCE: 11

Tyr Arg Pro Lys Pro Gln Gln Phe Phe Gly Leu Met
1               5                   10

<210> SEQ ID NO 12
<211> LENGTH: 8
<212> TYPE: PRT
<213> ORGANISM: Human

<400> SEQUENCE: 12

Pro Gln Gln Phe Phe Gly Leu Met
1               5

<210> SEQ ID NO 13
<211> LENGTH: 7
<212> TYPE: PRT
<213> ORGANISM: Human

<400> SEQUENCE: 13

Gln Gln Phe Phe Gly Leu Met
1               5

<210> SEQ ID NO 14
<211> LENGTH: 6
<212> TYPE: PRT
<213> ORGANISM: Human

<400> SEQUENCE: 14

Gln Phe Phe Gly Leu Met
1               5

<210> SEQ ID NO 15
<211> LENGTH: 5
<212> TYPE: PRT
<213> ORGANISM: Human

<400> SEQUENCE: 15

Phe Phe Gly Leu Met
1               5

<210> SEQ ID NO 16
<211> LENGTH: 5
<212> TYPE: PRT
<213> ORGANISM: Human

<400> SEQUENCE: 16

Tyr Phe Gly Leu Met
1               5

<210> SEQ ID NO 17
<211> LENGTH: 5
<212> TYPE: PRT
<213> ORGANISM: Human

<400> SEQUENCE: 17

Gly Phe Gly Leu Met
1               5
```

METHODS FOR TREATING A CORNEAL DISORDER AND PROMOTING SKIN WOUND HEALING

CROSS-REFERENCE TO RELATED APPLICATIONS

This application is a Divisional application of application Ser. No. 10/497,628 filed Jun. 3, 2004 (U.S. Pat. No. 7,232, 881), which is the United States national phase application of International Application PCT/JP02/12632 filed Dec. 3, 2002.

TECHNICAL FIELD

The present invention relates to a novel peptide containing the amino acid sequence represented by Ser-Ser-Ser-Arg (SEQ ID NO: 1), a pharmaceutical composition containing the peptide as the active ingredient, and a therapeutic agent of corneal disorders or an agent promoting skin wound healing which comprises a peptide containing the amino acid sequence represented by Ser-Ser-Ser-Arg (SEQ ID NO: 1) and a peptide containing the amino acid sequence represented by Phe-Gly-Leu-Met-NH$_2$ (SEQ ID NO: 2)as the active ingredients.

BACKGROUND OF THE INVENTION

Cornea is a transparent, non-vascular tissue having a diameter of about 1 cm and a thickness of about 1 mm. The transparency of cornea affects the visionary function. Various physiological and biochemical phenomena in cornea work functionally, mainly for the purpose of maintaining the transparency of cornea.

Corneal epithelial defects caused by various diseases such as corneal ulcer, corneal erosion, keratitis and dry eye is spontaneously repaired unless mixed infection is associated. When the repair is delayed or not completed or the epithelial defect is prolonged with some reason, however, not only the normal construction of corneal epithelium is badly affected but also even the constructions and functions of the corneal stroma and endothelium are damaged. The principle of the therapeutic methods according to the conventional art is passive. That is, the therapeutic methods include protecting the corneal surface from external stimulation to intend spontaneous extension of corneal epithelium for re-surfacing the defected area. Following the development of cell biology in recent years, factors involved in proliferation, migration, adhesion, extension and the like have been elucidated. It was reported that compounds promoting the extension of corneal epithelium play important roles in repairing corneal epithelial defects (Japanese Journal of Clinical Ophthalmology, 46, 738-743 (1992); Japanese Journal of Ophthalmologic Surgery, 5, 719-727 (1992)).

Meanwhile, insulin-like growth factor is one of growth factors regulating growth of normal human cells like epidermal growth factors, fibroblast growth factors, platelet-derived growth factors and transforming growth factors and includes insulin-like growth factor-I (referred to as "IGF-I" hereinafter) and insulin-like growth factor-II (referred to as "IGF-II" hereinafter). Recently, for example, it was reported that IGF-I stimulates the proliferation of thyroid cells (J. Biol. Chem., 264, 18485-18488 (1989)) and that IGF-II regulates the muscle growth and differentiation (Hum. Mol. Genet., 3, 1117-1121 (1994)). In the field of ophthalmology, it was disclosed that IGF-I, IGF-II and their functional derivatives promote the survival of retinal neurons (the publication of Japanese Patent Publication (Tokuhyo) 7-500839); that IGF-II is widely effective for the treatment of all types of wounds mainly including lesions made during keratoplasty (the publication of JP-A-63-233925); and that a solution containing the growth factors can be used to keep eye tissues such as cornea to be used for keratoplasty at their fresh state even in a circumstance at low a temperature (the publications of JP-A-5-25001 and JP-A-6-48901). Further, another disclosure is made about a gel composition containing a growth factor that the gel composition is generally effective for wound healing of for example the anterior segment of the eye (the publication of JP-A-2-112).

On the other hand, substance P is a polypeptide consisting of 11 amino acids and has actions such as vasodilatation, the smooth muscle contraction, the promotion of salivary gland secretion, and diuresis. In the field of ophthalmology, it is disclosed that substance P can improve abnormal secretion of the goblet cells of conjunctiva (the publication of International Publication WO95/13087), while the kinetics of substance P in the case of inflammation such as keratitis is also reported (Nippon Ganka Gakkai Zasshi, 91, 982-987 (1987); Nippon Ganka Gakkai Zasshi, 92, 448-452 (1988); and the like). As described above, various studies have been done. Additionally, the publication of JP-A-10-17489 describes that the tetrapeptide Phe-Gly-Leu-Met-NH$_2$ (SEQ ID NO: 2) (referred to as "FGLM" hereinafter) on the C terminal of substance P when used in combination with IGF-I can promote wound healing of corneal epithelium and that the FGLM (SEQ ID NO: 2) is the minimum unit among partial peptides with such action of substance P. However, it has never been identified yet which amino acid sequence site in IGF-1 is responsible for the expression of the effect while IGF-1 is a polypeptide consisting of amino acids as many as 70.

Skin wounds are those of surface tissues, including a rupture, an abrasion, a surgical incision, a skin ulcer or a burn. Such skin wounds are treated by applying an emergency treatment to a wounded site and waiting for the wounds to spontaneously heal via the biological recovering power of their own. Such spontaneous healing requires a long time until recovery and pain continues during the term. Therefore, it is preferable that wound healing is actively promoted, by administering an agent for wound healing to wounded sites.

Because new epithelial tissues and connective tissues are formed through cell migration and growth in the course of wound healing, a pharmaceutical agent promoting or stimulating cell migration, differentiation and growth participating in wound healing is possibly an agent for wound healing. As such agent for wound healing, for example, lysozyme chloride and solcoseryl have been known.

However, the existent agents for wound healing do not have sufficient actions for promoting the wound healing so they are problematic in that they cannot completely heal wounds in a short period of time. It is considered that the cause is due to low contributions of these agents for wound healing to for example the re-surfacing of epidermis, collagen synthesis, the improvement of peripheral circulation, granulation, and angiogenesis, which are important elements in the course of wound healing.

There is no report about the minimum unit for exhibiting the activity in IGF-I and there is no report about the peptide per se of the amino acid sequence represented by Ser-Ser-Ser-Arg (SEQ ID NO: 1). Additionally, there is no report about the action of a joint administration of a peptide containing the amino acid sequence represented by Ser-Ser-Ser-Arg (SEQ ID NO: 1) and a peptide containing the amino acid sequence represented by Phe-Gly-Leu-Met-NH$_2$ (SEQ ID NO: 2) for corneal disorders or the action thereof for skin diseases.

Generally, peptides consisting of numerous amino acids when administered into biological organisms are apt to be cut owing to metabolism and the like. Additionally at a stage of their formulation for use as pharmaceutical agents, the peptides are apt to be decomposed. It is desired that a peptide should have a chain as short as possible. Because the pharmacological activity thereof should be retained, however, it is an important subject in the development of pharmaceutical products to find the minimum unit for the exhibition of the activity of a long-chain peptide. IGF-I is a long-chain peptide consisting of amino acids as many as 70. It is a very important subject for the preparation of a more useful pharmaceutical product to find the minimum unit for the exhibition of the activity of IGF-I. Still additionally, it is a very interesting subject to make studies about specific pharmacological actions, namely the action on corneal disorders and the action on skin wounds, using the minimum unit for the exhibition of the activity.

DISCLOSURE OF THE INVENTION

The present inventors found that the minimum unit for the exhibition of the activity of IGF-I was the amino acid sequence represented by Ser-Ser-Ser-Arg (SEQ ID NO: 1) (referred to as "SSSR" hereinafter), by synthesizing various partial peptides of IGF-I and carrying out a pharmacological test about the extension of corneal epithelium, administering substance P or FGLM (SEQ ID NO: 2) in combination with the partial peptides. The inventors also found that the joint administration of a peptide containing the amino acid sequence represented by SSSR (SEQ ID NO: 1) and substance P or FGLM (SEQ ID NO: 2) could promote the curing of corneal disorders and skin wound healing. Specifically, the inventors found that a composition containing (1) a peptide consisting of the amino acid sequence represented by Ser-Ser-Ser-Arg (SEQ ID NO: 1), or an analog thereof or pharmaceutically acceptable salts thereof and (2) a peptide consisting of the amino acid sequence represented by Phe-Gly-Leu-Met-NH$_2$ (SEQ ID NO: 2), or an analog thereof or pharmaceutically acceptable salts thereof was useful as a therapeutic agent for corneal disorders such as corneal ulcer, corneal erosion, keratitis or dry eye, where the cornea is at a damaged state because of various factors and as a curing agent of skin wounds such as a rupture, an abrasion, a surgical incision, a skin ulcer or a burn and gangrene caused by them. Herein, the therapeutic agent for corneal disorders and the skin wounds healing promoting agent in accordance with the invention may be used in blend with ascorbic acid, ascorbic acid esters, ascorbic acid salts, pantothenic acid and pantothenic acid salts and the like, with their wound healing action having already been known.

IGF-I is composed of individual domains, A, B, C and D. The domains A and B have a similar structure to those of insulin and IGF-II. With attention focused on the domains C and D of IGF-I, thus, the inventors examined the action of extending corneal epithelium. Then, the inventors carried out a corneal epithelium extension test, using the peptide composing the domain C or the peptide composing the domain D in combination with substance P. The inventors found that the peptide composing the domain C, namely Gly-Tyr-Gly-Ser-Ser-Ser-Arg-Arg-Ala-Pro-Gln-Thr (SEQ ID NO: 3) (referred to as "GYGSSSRRAPQT" hereinafter) had the activity. Even after two amino acids were then removed from the two ends of GYGSSSRRAPQT (SEQ ID NO: 3) respectively, the activity still remained. Thus, the amino acids in Gly-Ser-Ser-Ser-Arg-Arg-Ala-Pro (SEQ ID NO: 4) (referred to as "GSSSRRAP" hereinbelow) were sequentially substituted with alanine, using the alanine scanning approach, to synthesize alanine-substituted amino acid sequences. In the presence of substance P or FGLM (SEQ ID NO: 2) with the alanine-substituted amino acid sequences, then, a corneal epithelium extension test was carried out. Because all the peptides containing the amino acid sequence represented by SSSR (SEQ ID NO: 1) exhibited the activity, it was found that SSSR (SEQ ID NO: 1) was the essential, minimum partial peptide of IGF-I for the exhibition of the action for corneal epithelium extension.

The inventors principally achieved the following four inventions.

A first invention relates to a novel peptide consisting of the amino acid sequence represented by Ser-Ser-Ser-Arg (SEQ ID NO: 1), or a derivative thereof or pharmaceutically acceptable salts thereof.

The feature of the first invention is based on the finding of the novel peptide as the minimum unit for the activity exhibition of IGF-I, namely the novel peptide consisting of the amino acid sequence represented by Ser-Ser-Ser-Arg (SEQ ID NO: 1). Thus, the term peptide consisting of the amino acid sequence represented by Ser-Ser-Ser-Arg (SEQ ID NO: 1) or a derivative thereof (the peptide and a derivative thereof are collectively referred hereinbelow to as "SSSR derivative") means any novel peptide containing the amino acid sequence represented by Ser-Ser-Ser-Arg (SEQ ID NO: 1), with no specific limitation. The derivative of the peptide means the peptide represented by Ser-Ser-Ser-Arg (SEQ ID NO: 1) to which one or plural amino acids with no influence of the activity exhibition are preliminarily bound, the peptide with the N terminal protected with protective groups widely used for peptides, such as acyl group, the peptide with the C terminal protected with protective groups widely used for peptides, such as ester and amide. Additionally, the term derivative also includes the peptide with the hydroxyl group in the Ser residue being protected with common protective groups or with the amino group in the Arg residue being protected with common protective groups. More specifically, the SSSR (SEQ ID NO: 1) derivative includes for example SSSR (SEQ ID NO: 1) and GSSSRRAP (SEQ ID NO: 4) and additionally includes for example Ser-Ser-Ser-Arg-Arg (SEQ ID NO: 5) (abbreviated as "SSSRR" hereinbelow), Gly-Ser-Ser-Ser-Arg (SEQ ID NO: 6) (abbreviated as "GSSSR" hereinbelow), Gly-Ser-Ser-Ser-Arg-Arg (SEQ ID NO: 7) (abbreviated as "GSSSRR" hereinbelow), Ala-Ser-Ser-Ser-Arg-Arg-Ala-Pro (SEQ ID NO: 8) (abbreviated as "ASSSRRAP"), Gly-Ser-Ser-Ser-Arg-Ala-Ala-Pro (SEQ ID NO: 9) (abbreviated as "GSSSRAAP" hereinbelow) and Gly-Ser-Ser-Ser-Arg-Ala-Ala-Ala-Pro (SEQ ID NO: 10) (abbreviated as "GSSSRAAAP" hereinbelow). The amino acids composing these peptides are in L forms, D forms and DL forms, which are also encompassed within the scope of the invention. As specifically described in the section pharmacological test, all SSSR (SEQ ID NO: 1) derivatives containing the amino acid sequence represented by SSSR in the peptide chains when used in combination with substance P or FGLM (SEQ ID NO: 2) can exhibit the effect of extending corneal epithelium and the effect of promoting the skin wound healing.

The SSSR (SEQ ID NO: 1) derivatives of the invention can be prepared by known methods using an automatic peptide synthesizer, and the details are described in the Examples.

A second invention relates to a pharmaceutical composition containing the novel peptide consisting of the amino acid sequence represented by Ser-Ser-Ser-Arg (SEQ ID NO: 1) or a derivative thereof or pharmaceutically acceptable salts thereof as an active ingredient and being blended with a pharmaceutically acceptable additive.

A third invention relates to an agent for treating a corneal disorder, the agent containing (1) a peptide consisting of the amino acid sequence represented by Ser-Ser-Ser-Arg (SEQ ID NO: 1) or an analog thereof or pharmaceutically acceptable salts thereof and (2) a peptide consisting of the amino acid sequence represented by Phe-Gly-Leu-Met-NH$_2$ (SEQ ID NO: 2) or an analog thereof or pharmaceutically acceptable salts thereof as active ingredients.

A fourth invention relates to an agent for promoting skin wound healing, the agent containing the peptide (1) and the peptide (2) as active ingredients.

The feature of the third and fourth inventions is the finding that the joint administration of the peptide where the minimum unit for the exhibition of the activity is represented by Ser-Ser-Ser-Arg (SEQ ID NO: 1) and the peptide where the minimum unit for the exhibition of the activity is represented by Phe-Gly-Leu-Met-NH$_2$ (SEQ ID NO: 2), can exhibit a excellent effect of extending corneal epithelium and also a excellent effect of promoting skin wound healing.

In the third and fourth inventions, the term peptide consisting of the amino acid sequence represented by Ser-Ser-Ser-Arg (SEQ ID NO: 1) or an analog thereof (the peptide and an analog thereof are collectively referred to as "SSSR analog" hereinafter) means any peptide containing the amino acid sequence represented by Ser-Ser-Ser-Arg (SEQ ID NO: 1), with no specific limitation. The analog of the peptide means the peptide represented by Ser-Ser-Ser-Arg (SEQ ID NO: 1) to which one or plural amino acids with no influence of the activity exhibition are preliminarily bound, the peptide with the N terminal protected with protective groups widely used for peptides, such as acyl group, the peptide with the C terminal protected with protective groups widely used for peptides, such as ester and amide. Additionally, the term SSSR (SEQ ID NO: 1) analog also includes the peptide with the hydroxyl group in the Ser residue being protected with common protective groups or with the amino group in the Arg residue being protected with common protective groups. More specifically, the SSSR (SEQ ID NO: 1) analog includes for example the SSSR (SEQ ID NO: 1) derivatives described above and GYGSSSRRAPQT (SEQ ID NO: 3). The amino acids composing the peptide of the SSSR (SEQ ID NO: 2) analog are in L forms, D forms and DL forms, which are all encompassed within the scope of the invention. A more preferable mode is a peptide composed of amino acids all in L forms.

Still additionally, the term peptide consisting of the amino acid sequence represented by Phe-Gly-Leu-Met-NH$_2$ (SEQ ID NO: 2) or an analog thereof (the peptide and the analog thereof are collectively referred to as "FGLM analog" hereinafter) means any peptide containing the amino acid sequence represented by Phe-Gly-Leu-Met-NH$_2$ (SEQ ID NO: 2), with no specific limitation. The analog of the peptide means the peptide represented by Phe-Gly-Leu-Met-NH$_2$ (SEQ ID NO: 2) to which one or plural amino acids with no influence of the activity exhibition are preliminarily bound, and the peptide with the N terminal protected with protective groups widely used for peptides, such as acyl group. More specifically, the FGLM (SEQ ID NO: 2) analog includes for example substance P and FGLM (SEQ ID NO: 2) and additionally includes the following polypeptides composed of four to 12 amino acids as disclosed in U.S. Pat. No. 3,862,114:

Tyr-Arg-Pro-Lys-Pro-Gln-Gln-Phe-Phe-Gly-Leu-Met-NH$_2$; (SEQ ID NO: 11)

Pro-Gln-Gln-Phe-Phe-Gly-Leu-Met-NH$_2$; (SEQ ID NO: 12)

Gln-Gln-Phe-Phe-Gly-Leu-Met-NH$_2$; (SEQ ID NO: 13)

Gln-Phe-Phe-Gly-Leu-Met-NH$_2$; (SEQ ID NO: 14)

Phe-Phe-Gly-Leu-Met-NH$_2$; (SEQ ID NO: 15)

Tyr-Phe-Gly-Leu-Met-NH$_2$; (SEQ ID NO: 16)
and

Gly-Phe-Gly-Leu-Met-NH$_2$. (SEQ ID NO: 17)

A preferable example thereof includes substance P and FGLM (SEQ ID NO: 2). Amino acids composing them are in L forms, D forms and DL forms. They are all encompassed within the scope of the invention. A more preferable mode is a peptide composed of amino acids all in L forms.

In accordance with the invention, pharmaceutically acceptable salts thereof include for example hydrochloride salt, sulfate salt, phosphate salt, lactate salt, maleate salt, fumarate salt, oxalate salt, methanesulfonate salt, and p-toluenesulfonate salt.

In accordance with the invention, the joint administration of the SSSR (SEQ ID NO: 1) analog and the FGLM (SEQ ID NO: 2) analog exhibits actions of extending corneal epithelium and promoting the skin wound healing. Any types of the SSSR (SEQ ID NO: 1) analog and the FGLM (SEQ ID NO: 2) analog exhibiting these actions are satisfactory with no specific limitation. The joint administration of SSSR (SEQ ID NO: 1) as the minimum unit of the activity exhibition of IGF-I and FGLM (SEQ ID NO: 2) as the minimum unit of the activity exhibition of substance P is preferable for carrying out the invention.

The agent for treating corneal disorders and the agent for promoting the skin wound healing in accordance with the invention can be prepared using common techniques. The SSSR (SEQ ID NO: 1) analog or pharmaceutically acceptable salts thereof and the FGLM (SEQ ID NO: 2) analog or pharmaceutically acceptable salts thereof are individually formulated into single formulations or formulated into blend formulations, which may be administered parenterally or orally. Parenteral administration thereof is more preferable.

Preferable dosage forms of the agent for treating corneal disorders include for example eye drops and eye ointments. These can be prepared using common techniques. For example, the eye drops can be prepared, using isotonic agents such as sodium chloride, buffers such as sodium phosphate, and preservatives such as benzalkonium chloride. The pH is satisfactory if it is within an ophthalmologically acceptable range. Preferred pH is within pH 4 to 8.

The dose of the agent for treating corneal disorders is appropriately selected, depending on the symptoms, age of patients, dosage form and the like. For eye drops, the concentration of the SSSR (SEQ. ID NO: 1) analog or pharmaceutically acceptable salts thereof is 0.001 to 10 w/v %, preferably 0.01 to 1 w/v % for administration into eyes once or several times a day. The concentration of the FGLM (SEQ ID NO: 2) analog or pharmaceutically acceptable salts thereof is 0.00001 to 0.1 w/v %, preferably 0.0001 to 0.01 w/v % for administration into eyes once or several times a day.

It is needless to say that both the active ingredients are blended together to prepare formulations such as eye drops.

Preferable forms of the formulation of the agent for promoting the skin wound healing include for example an ointment, a jelly, a cataplasm, a patch, a lotion, a cream, a spray, an aerosol, a plaster, a suspension and an emulsion. Additionally, a liquid can be prepared by selecting an appropriate solvent. So as to prepare the agent for promoting the skin wound healing, the following agents can be added, depending on the dosage form: fillers, excipients, bases or vehicles, expanders, pH adjusters, solubilizers, suspending agents, buffers, stabilizers, preservatives, surfactants, anti-oxidants, dispersants, emulsifying agents, dissolution agents and auxiliary agents for dissolution.

The carrier for the formulation includes for example white Vaseline, fluid paraffin, gelled hydrocarbon, cetyl alcohol, polyethylene glycol, gelatin, corn starch, sodium alginate, methyl cellulose, hydroxyethyl cellulose, carboxymethyl cellulose, plastibase hydrophilic, gelatin, dextrin, cetyl alcohol, stearyl alcohol, polyethylene glycol, polyvinyl alcohol, methoxyethylene-maleic anhydride copolymer, polyvinyl ether, and polymers and copolymers with a constitutional component of vinyl pyrrolidone, sodium stearate, magnesium stearate, benzalkonium chloride, fats and oils such as olive oil, camellia oil, and soybean oil, lactose and water.

The agent for promoting the skin wound healing in accordance with the invention can be administered in various forms, depending on the wound site and the wounded level. In case that the agent is to be used as an external preparation, the agent is preferably directly coated, sprayed or attached on a necessary site (lesion) such as skin.

The dose of the agent for promoting the skin wound healing in accordance with the invention can be selected appropriately, in terms of the symptoms, age of patients, dosage form and the like. The dose of the SSSR (SEQ ID NO: 1) analog or pharmaceutically acceptable salts thereof is generally 0.001 to 1000 mg, preferably 0.01 to 500 mg per day, in one portion or in several portions. Additionally, the dose of the FGLM (SEQ ID NO: 2) analog or pharmaceutically acceptable salts thereof is generally 0.01 to 5000 mg, preferably 0.1 to 1000 mg per day, in one portion or in several portions.

It is needless to say that both the active ingredients are blended together to prepare formulations such as ointments.

Preparation examples, formulation examples and the results of a pharmacological test are shown below. These are for better understanding of the invention but never limit the scope of the invention.

BEST MODE FOR CARRYING OUT THE INVENTION

Preparation Examples

Representative preparation examples of the SSSR analog for use in the invention are shown below.

1. SSSR (SEQ ID NO: 1) Preparation

Using an automatic peptide synthesizer 430A (manufactured by Applied Biosystems) and according to an existent software, a protective peptide resin was synthesized by the tertiary butyloxycarbonyl (BOC) method. As a starting raw material, 4-(oxymethyl)phenylacetoamide methyl [Boc-Arg (Tos) PAM] resin carrier (0.5 mmol scale) was used. In this synthetic method, 30% trifluoroacetic acid (TFA)/dichloromethane and 70% TFA/dichloromethane were used for the removal of Boc group as a Na-amino protective group. For rinsing, N-methyl-2-pyrrolidone (NMP)/dichloromethane was used. N,N'-Dicyclohexylcarbodiimide (DCC) and 1-hydroxybenzotriazole (HOBt) as condensing agents and the Boc-Ser (OBzl) derivative as an N-protected amino acid are used at 4 equivalents per amino group respectively, while dimethylsulfoxide (DMSO)-NMP (8:2) was used as a reaction solvent. After completion of the condensation, the generation of defective peptides was prevented with acetic anhydride/N,N-diisopropylethylamine (DIEA) to completely block the remaining amino groups. The removal of the Boc group and the condensation of Boc-Ser (OBzl) were repeated to construct the final protected peptide. The scissoring out of the peptide from the resulting protected peptide resin and the elimination of all the protective groups were carried out by a process with anhydrous hydrogen fluoride (HF) (HF: p-cresol=8:2 (v/v); −2 to −5° C.; 60 minutes). After the reaction, HF was distilled away, and the peptide was extracted with aqueous 0.1% trifluoroacetic acid. A crude product was obtained as a freeze-dried powder, for preparative separation and purification. The preparative separation and purification was done on a 0.5 to 2% gradient of an acetonitrile/water system (containing 0.1% TFA), using HPLC LC8A (manufactured by Shimadzu Corporation) (column: ODS 30×240 mm manufactured by YMC) (80 minutes). After collecting highly pure fractions of the resulting objective material and distilling acetonitrile away from the material, the resulting material was freeze-dried to obtain the TFA salt of the target compound (70 mg; yield of 32%). Amino acid analysis (conditions for hydrolysis: 6N HCl, 110° C., 22 hours)

Ser(3) 2.74, Arg (1) 1.00

HPLC analysis [Column: YMC Pak ODS-A (4.6 mm I.D.× 150 mm); Eluent: 1-60% $CH_3CN$/5 mM $CF_3CF_2COOH$ (25 min); Temp.: 25° C.; Flow rate: 1.0 ml/min: Detector: 220 nm].

Purity (HPLC): 98.5%

Mass analysis (ESI-MS)

$MH^+$=436.2 (Theor.=436.2, mono isotopic)

2. Preparation of SSSR (SEQ ID NO: 1) Analog

The same procedures for SSSR (SEQ ID NO: 1) were repeated to prepare GSSSR (SEQ ID NO: 6), SSSRR (SEQ ID NO: 5), GSSSRR (SEQ ID NO: 7), GSSSRRAP (SEQ ID NO: 4), ASSSRRAP (SEQ ID NO: 8), GSSSRAAP (SEQ ID NO: 9) and GSSSRAAAP (SEQ ID NO: 10). The physical properties of representative peptides are shown below.

(1)        GSSSR        (SEQ ID NO: 6)

Amino acid analysis (conditions for hydrolysis: 6N HCl, 110° C., 22 hours)

Ser(3) 2.76, Gly (1) 1.00, Arg (1) 1.00

HPLC analysis [Column: YMC Pak ODS-A (4.6 mm I.D.× 150 mm); Eluent: 1-60% $CH_3CN$/5 mM $CF_3CF_2COOH$ (25 min); Temp.: 25° C.; Flow rate: 1.0 ml/min: Detector: 220 nm].

Purity (HPLC): 98.5%

Mass analysis (ESI-MS)

MW=492.3 (Theor.=492.5)

(2)        SSSRR        (SEQ ID NO: 5)

Amino acid analysis (conditions for hydrolysis: 6N HCl, 110° C., 22 hours)

Ser(3) 2.76, Arg (2) 2.00

HPLC analysis [Column: YMC Pak ODS-A (4.6 mm I.D.× 150 mm); Eluent: 1-60% CH$_3$CN/0.1% CF$_3$COOH (25 min); Temp.: 25° C.; Flow rate: 1.0 ml/min: Detector: 220 nm].

Purity (HPLC): 99.7%

Mass analysis (ESI-MS)

MW=591.5 (Theor.=591.6)

(3) GSSSRR (SEQ ID NO: 7)

Amino acid analysis (conditions for hydrolysis: 6N HCl, 110° C., 22 hours)

Ser(3) 2.73, Gly(1) 0.98, Arg (2) 2.00

HPLC analysis [Column: YMC Pak ODS-A (4.6 mm I.D.× 150 mm); Eluent: 1-60% CH$_3$CN/0.1% CF$_3$COOH (25 min); Temp.: 25° C.; Flow rate: 1.0 ml/min: Detector: 220 nm].

Purity (HPLC): 99.3%

Mass analysis (ESI-MS)

MW=648.5 (Theor.=648.7)

(4) GSSSRRAP (SEQ ID NO: 4)

Amino acid analysis (conditions for hydrolysis: 6N HCl, 110° C., 22 hours)

Ser(3) 2.68, Gly(1) 0.99, Ala(1) 1.01, Arg (2) 2.00

HPLC analysis [Column: YMC Pak ODS-A (4.6 mm I.D.× 150 mm); Eluent: 1-60% CH$_3$CN/0.1% CF$_3$COOH (25 min); Temp.: 25° C.; Flow rate: 1.0 ml/min: Detector: 220 nm].

Purity (HPLC): 98.6%

Mass analysis (ESI-MS)

MW=816.7 (Theor.=816.9)

Formulation Examples

Representative formulation examples for use in accordance with the invention are shown below.

1. Eye Drop

An eye drop of the following formulation was prepared by a wide method.

Formulation Example 1

| | |
|---|---|
| SSSR (SEQ ID NO: 1) | 1 mg |
| Sodium chloride | 900 mg |
| Sodium hydroxide | quantum sufficient |
| Hydrochloric acid | quantum sufficient |
| Sterile purified water In 100 ml | quantum sufficient |

In the same manner as for the Formulation Example 1, eye drops containing SSSR (SEQ ID NO: 1) of 0.01 mg, 0.05 mg, 0.1 mg, 0.5 mg, 5 mg, 10 mg, 50 mg and 100 mg in 100 ml can be prepared.

2. Formulation Example 2

| | |
|---|---|
| GSSSR (SEQ ID NO: 6) | 1 mg |
| FGLM (SEQ ID NO: 2) | 100 mg |
| Sodium chloride | 900 mg |
| Sodium hydroxide | quantum sufficient |
| Hydrochloric acid | quantum sufficient |
| Sterile purified water In 100 ml | quantum sufficient |

In the same manner as for the Formulation Example 2, eye drops containing FGLM (SEQ ID NO: 2) of 1 mg, 5 mg, 10 mg, 50 mg, 500 mg, and 1000 mg in 100 ml can be prepared.

Formulation Example 3

| | |
|---|---|
| SSSR (SEQ ID NO: 1) | 1 mg |
| FGLM (SEQ ID NO: 2) | 100 mg |
| Sodium chloride | 900 mg |
| Sodium hydroxide | quantum sufficient |
| Hydrochloric acid | quantum sufficient |
| Sterile purified water In 100 ml | quantum sufficient |

In the same manner as for the Formulation Example 3, eye drops containing SSSR (SEQ ID NO: 1) of 0.01 mg, 0.05 mg, 0.1 mg, 0.5 mg, 10 mg, 50 mg and 100 mg and FGLM (SEQ ID NO: 2) of 1 mg, 5 mg, 10 mg, 50 mg, 500 mg and 1000 mg in optional combinations can be prepared.

2. Ointment

Formulation Example 4

| | |
|---|---|
| SSSR (SEQ ID NO: 1) | 10 mg |
| FGLM (SEQ ID NO:2) | 100 mg |
| Liquid paraffin | 10 g |
| White Vaseline In 100 g | quantum sufficient |

By appropriately modifying the amount of SSSR (SEQ ID NO: 1) to be added and the amount of FGLM (SEQ ID NO: 2) to be added, various concentrations of ointments can be prepared.

Formulation Example 5

```
GSSSR                    1 mg
(SEQ ID NO: 6)

Substance P              100 mg

Liquid paraffin          10 g

White Vaseline           quantum sufficient
In 100 g
```

By appropriately modifying the amount of GSSSR (SEQ ID NO: 6) to be added and the amount of substance P to be added in the same manner as for the Formulation Example 5, various concentrations of ointments can be prepared.

```
Formulation Example 6
SSSRR                    5 mg
(SEQ ID NO: 5)

FGLM                     100 mg
(SEQ ID NO: 2)

Liquid paraffin          10 g

White Vaseline           quantum sufficient
In 100 g
```

By appropriately modifying the amount of SSSRR (SEQ ID NO: 5) to be added and the amount of FGLM (SEQ ID NO: 2) to be added, various concentrations of ointments can be prepared.

Formulation Example 7

```
GSSSRR                   50 mg
(SEQ ID NO: 7)

Substance P              10 mg

Ascorbic acid            3 mg

Liquid paraffin          10 g

Plastibase hydrophilic   quantum sufficient
In 100 g
```

By appropriately modifying the amount of GSSSRR (SEQ ID NO: 7) to be added and the amount of substance P to be added, various concentrations of ointments can be prepared.

<Pharmacological Test>

(1) Action For Extending Corneal Epithelium (In Vitro)

Using the cornea of a male Japanese White rabbit and according to the method of Nishida et al. (J. Cell Biol., 97, 1653-1657 (1983)), the length of corneal epithelium extension of the corneal section in a tissue culture system was used as a marker to examine the influence on corneal epithelium extension.

Experimental Method

Corneal blocks cut off from rabbit corneal section (6 blocks per group) were cultured in culture media (TC-199) containing a test compound under conditions of 5% $CO_2$ at 37° C. for 24 hours. After culturing, the corneal blocks were fixed in a mix solution of ethanol-glacial acetic acid (volume ratio: 95:5) and then embedded in paraffin to prepare sections. After paraffin was removed from the sections, the resulting sections were stained with hematoxylin-eosin to examine the extended length of the corneal epithelial cell layer with a microscope. As a control, the blocks cultured in the same manner in the culture media without any test compound were used.

Test Compounds

Representative examples of the peptides used in the experiment are shown in Table 1.

Results

The experimental results are shown in Table 1. Herein, the extension ratio in the table is the mean of six sections per group, as calculated when the elongated length of the control group was defined as the basal line (100%).

TABLE 1

| Test drugs | Extension ratio (%) |
|---|---|
| Control | 100 |
| SSSR (SEQ ID NO: 1) (1 nM) | 101 |
| GSSSR (SEQ ID NO: 6) (1 nM) | 101 |
| SSSRR (SEQ ID NO: 5) (1 nM) | 98 |
| GSSSRR (SEQ ID NO: 7) (1 nM) | 94 |
| GSSSRRAP (SEQ ID NO: 4) (1 nM) | 97 |
| GSSSRAAAP (SEQ ID NO: 10) (1 nM) | 100 |
| GYGSSSRRAPQT (SEQ ID NO: 3) (1 nM) | 104 |
| Substance P (20 μM) | 94 |
| FGLM (SEQ ID NO: 2) (20 μM) | 99 |
| SSSR (SEQ ID NO: 1) (1 nM) + substance P (20 μM) | 138 |
| GSSSR (SEQ ID NO: 6) (1 nM) + substance P (20 μM) | 135 |
| SSSRR (SEQ ID NO: 5) C1 nM) + substance P (20 μM) | 136 |
| GSSSRR (SEQ ID NO: 7) (1 nM) + substance P (20 μM) | 142 |
| GSSSRRAP (SEQ ID NO: 4) (1 nM) + substance P (20 μM) | 140 |
| ASSSRRAP (SEQ ID NO: 8) (1 nM) + substance P (20 μM) | 134 |
| GSSSRAAP (SEQ ID NO: 9) (1 nM) + substance P (20 μM) | 150 |

TABLE 1-continued

| Test drugs | Extension ratio (%) |
|---|---|
| GSSSRAAAP (SEQ ID NO: 10) (1 nM) + substance P (20 μM) | 139 |
| GYGSSSRRAPQT (SEQ ID NO: 3) (1 nM) + substance P (20 μM) | 134 |
| SSSR (SEQ ID NO: 1) (1 nM) + FGLM (SEQ ID NO: 2) (20 μM) | 145 |

As shown in Table 1, the SSSR (SEQ ID NO: 1) analogs alone, substance P alone and FGLM (SEQ ID NO: 2) alone were not observed to have any influence on the extension of corneal epithelium; however, it was observed that the extension of corneal epithelium was significantly promoted when the corneal epithelium was cultured in the culture medium containing both the SSSR (SEQ ID NO: 1)analog and substance P (or FGLM (SEQ ID NO: 2)).

(2) Action On Healing Skin Wounds

The action of healing skin wounds can be tested by the following method.

A rat is anesthetized under inhalation of diethyl ether; then, the dorsal hair is razored with hair clippers and then removed with a depilatory cream. 24 hours later, five wound sites throughout all the layers of epidermis and dermis are made at an equal interval on the dorsal skin, using a trephine of a 5 mm diameter for dermal biopsy. After hemostasis was confirmed, an SSSR (SEQ ID NO: 1)-containing ointment, an FGLM (SEQ ID NO: 2)-containing ointment and anointment containing SSSR (SEQ ID NO: 1) and FGLM (SEQ ID NO: 2) are individually applied once daily. Before the application of the individual ointments, the dorsal wounds of the rat are photographed and measured of their areas. The areas of the individual wounds after applied with the SSSR (SEQ ID NO: 1)-containing ointment, the FGLM (SEQ ID NO: 2)-containing ointment and the ointment containing SSSR (SEQ ID NO: 1) and FGLM (SEQ ID NO: 2) are compared to each other, to examine the effect of healing skin wounds.

INDUSTRIAL APPLICABILITY

Based on the results of the pharmacological test, a joint administration of the SSSR (SEQ ID NO: 1) analog containing the amino acid sequence represented by Ser-Ser-Ser-Arg (SEQ ID NO: 1) as the minimum unit for the exhibition of the activity of IGF-I and the FGLM (SEQ ID NO: 2) analog containing the amino acid sequence represented by Phe-Gly-Leu-Met-$NH_2$ (SEQ ID NO: 2) significantly promotes the extension of corneal epithelium and the healing skin wounds. Thus, the SSSR (SEQ ID NO: 1) analog and the FGLM (SEQ ID NO: 2) analog when administered in combination synergistically act to exhibit effects as therapeutic agents of corneal disorders such as corneal ulcer, corneal erosion, keratitis and dry eye or effects as healing agents of skin wounds such as a rupture, an abrasion, a surgery incision, a skin ulcer and a burn and diseases due to them, such as gangrene.

What is claimed is:

1. A method for treating a corneal disorder comprising administering to a patient in need thereof a composition containing pharmaceutically effective amounts of (i) a peptide of which the amino acid sequence is Ser-Ser-Ser-Arg (SEQ ID NO: 1), Gly-Tyr-Gly-Ser-Ser-Ser-Arg-Arg-Ala-Pro-Gln-Thr (SEQ ID NO: 3), Gly-Ser-Ser-Ser-Arg-Arg-Ala-Pro (SEQ ID NO: 4), Ser-Ser-Ser-Arg-Arg (SEQ ID NO: 5), Gly-Ser-Ser-Ser-Arg (SEQ ID NO: 6), Gly-Ser-Ser-Ser-Arg-Arg (SEQ ID NO: 7), Ala-Ser-Ser-Ser-Arg-Arg-Ala-Pro (SEQ ID NO: 8), Gly-Ser-Ser-Ser-Arg-Ala-Ala-Pro (SEQ ID NO: 9), Gly-Ser-Ser-Ser-Arg-Ala-Ala-Ala-Pro (SEQ ID NO: 10) or a pharmaceutically acceptable salt thereof and (ii) a peptide of which the amino acid sequence is —NH$_2$ Phe-Gly-Leu-Met-NH$_2$ (SEQ ID NO: 2), substance P or a pharmaceutically acceptable salt thereof, together with a pharmaceutically acceptable carrier.

2. The method according to claim 1, wherein the corneal disorder is a corneal ulcer, a corneal erosion, keratitis or dry eye.

3. The method according to claim 2, wherein the composition is administered in a dosage form which is an eye drop.

4. A method for treating a corneal disorder comprising administering to a patient in need thereof a composition containing pharmaceutically effective amounts of (i) a peptide of which the amino acid sequence is Ser-Ser-Ser-Arg (SEQ ID NO: 1), or a pharmaceutically acceptable salt thereof and (ii) a peptide of which the amino acid sequence is Phe-Gly-Leu-Met-NH$_2$ (SEQ ID NO: 2), or a pharmaceutically acceptable salt thereof, together with a pharmaceutically acceptable carrier.

5. The method according to claim 4, wherein the corneal disorder is a corneal ulcer, a corneal erosion, keratitis or dry eye.

6. The method according to claim 4, wherein the composition is administered in a dosage form which is an eye drop.

* * * * *